(12) United States Patent
Griffin et al.

(10) Patent No.: US 8,882,925 B2
(45) Date of Patent: Nov. 11, 2014

(54) METHOD FOR SCALE REMOVAL DURING A LIGNOCELLULOSIC CONVERSION PROCESS

(75) Inventors: Robert Griffin, Ontario (CA); Vladimir Pavlovic, Ontario (CA); Daphne Wahnon, Ontario (CA)

(73) Assignee: Iogen Energy Corporation, Ontario (CA)

( * ) Notice: Subject to any disclaimer, the term of this patent is extended or adjusted under 35 U.S.C. 154(b) by 177 days.

(21) Appl. No.: 13/522,069

(22) PCT Filed: Feb. 8, 2011

(86) PCT No.: PCT/CA2011/000149
§ 371 (c)(1),
(2), (4) Date: Sep. 5, 2012

(87) PCT Pub. No.: WO2011/094859
PCT Pub. Date: Aug. 11, 2011

(65) Prior Publication Data
US 2012/0325203 A1 Dec. 27, 2012

Related U.S. Application Data

(60) Provisional application No. 61/302,338, filed on Feb. 8, 2010.

(51) Int. Cl.
| | |
|---|---|
| C13K 13/00 | (2006.01) |
| C08H 7/00 | (2011.01) |
| D21C 9/00 | (2006.01) |
| D21C 5/00 | (2006.01) |
| C13K 1/02 | (2006.01) |
| C08H 8/00 | (2010.01) |
| D21C 9/08 | (2006.01) |

(52) U.S. Cl.
CPC .. *C13K 1/02* (2013.01); *C08H 6/00* (2013.01); *C12P 2201/00* (2013.01); *D21C 9/083* (2013.01); *D21C 9/008* (2013.01); *D21C 5/005* (2013.01); *C08H 8/00* (2013.01); *Y02E 50/16* (2013.01)
USPC .......................................................... 127/37

(58) Field of Classification Search
None
See application file for complete search history.

(56) References Cited

U.S. PATENT DOCUMENTS

| | | | |
|---|---|---|---|
| 2,390,695 | A | 12/1945 | Dean et al. |
| 3,546,200 | A | 12/1970 | Whalen et al. |
| 3,849,328 | A | 11/1974 | Schievelbein et al. |
| 4,196,094 | A | 4/1980 | Johnson et al. |

(Continued)

FOREIGN PATENT DOCUMENTS

| | | |
|---|---|---|
| EP | 0 432 310 B1 | 6/1991 |
| EP | 0 540 934 B1 | 12/1993 |
| EP | 0921228 A2 | 6/1999 |
| EP | 1 026 312 A1 | 9/2000 |

(Continued)

OTHER PUBLICATIONS

Xu et al., "Lignin precipitation on the pulp fibers in the ethanol-based organosolv pulping", Colloids and Surfaces A: Physicochemical and Engineering Aspects, vol. 301, No. 103, (2007) 255-63.

(Continued)

*Primary Examiner* — Melvin C Mayes
*Assistant Examiner* — Stefanie Cohen
(74) *Attorney, Agent, or Firm* — Fitzpatrick, Cella, Harper & Scinto (57) ABSTRACT

A method for processing of a lignocellulosic feedstock is provided comprising exposing lignocellulosic feedstock to acid in a reactor to hydrolyze at least hemicellulose present in said lignocellulosic feedstock, wherein during said exposing, a scale deposit comprising lignin forms on the inner surface of said reactor; and treating the scale deposit with an alkali solution at a temperature between about 140° C. and about 250° C. so as to remove scale. Also provided is a method for reducing scale deposit that forms on process equipment during a stage of reacting a lignocellulosic feedstock with acid.

19 Claims, 4 Drawing Sheets

SOLUBLE LIGNIN CONCENTRATION AND SCALE DISSOLUTION AS A FUNCTION OF AGING TIME

(56) References Cited

U.S. PATENT DOCUMENTS

| | | | |
|---|---|---|---|
| 4,764,596 A | | 8/1988 | Lora et al. |
| 4,933,399 A | | 6/1990 | Shimizu et al. |
| 5,221,357 A | * | 6/1993 | Brink .............................. 127/43 |
| 7,465,791 B1 | | 12/2008 | Hallberg et al. |
| 2008/0121359 A1 | | 5/2008 | Holtzapple et al. |
| 2008/0277083 A1 | | 11/2008 | Shevchenko et al. |
| 2010/0024807 A1 | | 2/2010 | Burke et al. |

FOREIGN PATENT DOCUMENTS

| | | | |
|---|---|---|---|
| EP | 1908876 A1 | | 4/2008 |
| GB | 850367 | * | 10/1960 |
| WO | 97/15712 A2 | | 5/1997 |
| WO | 2006/128304 A1 | | 12/2006 |
| WO | 2007/095575 A1 | | 8/2007 |
| WO | 2007/129921 A1 | | 11/2007 |
| WO | 2010096510 A2 | | 8/2010 |

OTHER PUBLICATIONS

Shah et al., "Effect of Pretreatment on Simultaneous Saccharification and Fermentation of Hardwood into Acetone/Butanol", Applied Biochemistry and Biotechnology, vol. 28/29 (1991) 99-109.

Eriksson, "Concluding Remarks: Where Do We Stand and Where are we Going? Lignin Biodegradation and Practical Utilization", Journal of Biotechnology, vol. 30 (1991) 149-58.

Aden et al., Lignocellulosic Biomass to Ethanol Process Design and Economics Utilizing Co-Current Dilute Acid Prehydrolysis for Corn Stover, National Renewable Energy Laboratory, NREL/TP-510-32438, (2002) 39.

Selig et al., "Deposition of Lignin Droplets Produced During Dilute Acid Pretreatment of Maize Stems Retards Enzymatic Hydrolysis of Cellulose", Biotechnology Progress, vol. 23 (2007) 1333-39.

Brauns, Friedrich Emil, The Chemistry of Lignin, Academic Press Inc., New York (1952) 50-61, 111-19, 140-49, 182-88, 198-09.

Zhang, et al., "Removal of Residual Lignin of Ethanol-Based Organosolv Pulp by an Alkali Extraction Process", Journal of Applied Polymer Science, vol. 106 (2007) 630-36.

Gurram et al., "Analysis of heat transfer fouling characteristics during evaporation of clarified pine wood hydrolysate to concentrate sugars", 2010 AIChE Annual Meeting, Conference Proceedings, Salt Lake City, Utah, Nov. 2010, ISBN 978081690656.

* cited by examiner

METHOD FOR SCALE REMOVAL DURING A LIGNOCELLULOSIC CONVERSION PROCESS

This application is a national stage application of PCT/CA2011/000149 having an international filing date of Feb. 8, 2011, which claims benefit of U.S. provisional application No. 61/302,338 filed Feb. 8, 2010, both of which are incorporated by reference herein.

FIELD OF INVENTION

The present invention relates to a method for the processing of lignocellulosic feedstocks. More specifically, the present invention relates to a method of processing lignocellulosic feedstocks using acidic pretreatment.

BACKGROUND OF THE INVENTION

In recent years there has been an increasing interest in generating ethanol and fine chemicals from lignocellulosic feedstocks. These feedstocks are of particular interest as they are inexpensive and are often burned or landfilled. Accordingly, there is an enormous untapped potential for their use as a source of fermentable sugar to produce ethanol or other byproducts. The fermentable sugar is produced from the polysaccharide components of the feedstock, namely cellulose which makes up 30% to 50% of most of the key feedstocks, and hemicellulose which is present at 15% to 30% in most feedstocks. The remaining components of lignocellulosic feedstock include lignin, which is typically present at 15-30%, ash, protein and starch.

In order to produce sugar from lignocellulosic feedstocks, it is first necessary to break the polysaccharides down into their composite sugar molecules and this is typically accomplished by physical and/or chemical pretreatment, followed by hydrolysis of the cellulose. An example of a chemical pretreatment is acid pretreatment (see U.S. Pat. No. 4,461,648), which hydrolyzes most of the hemicellulose to xylose, galactose, mannose and arabinose, but results in little conversion of the cellulose to glucose. The cellulose may be hydrolyzed to glucose by cellulase enzymes or by further chemical treatment with acid.

It is also known to hydrolyze the lignocellulosic feedstock in a single step with acid that utilizes harsher conditions to effect hydrolysis of both the hemicellulose and cellulose components of the feedstock.

Glucose can be fermented to fuels including, but not limited to, ethanol or butanol or other chemicals, examples of which include sugar alcohols and organic acids. The pentose sugars, xylose and arabinose, can be fermented to ethanol by recombinant yeast (see U.S. Pat. No. 5,789,210 (Ho et al.), U.S. Pat. No. 5,126,266 (Jeffries et al.), WO 2008/130603 (Abbas et al.) and WO 03/095627 (Boles and Becker)) or by bacteria. Moreover, the production of xylitol from xylose has received much attention because of its value as a substitute sugar sweetener.

The development of a continuous process to produce ethanol or other fermentation products that can be operated and maintained economically has been the goal of various researchers in the field. Reductions in throughput compromise productivity, which can translate into significant cost. To maintain a continuous, high throughput process, the flow rate throughout the process should be consistent. If the flow rate through one stage of the process is reduced, subsequent stages are similarly affected, which ultimately reduces the throughput of the entire system. Moreover, interruptions to the process can also significantly reduce the efficiency of the process.

It was unexpectedly discovered that a solid scale deposit (referred to herein as "scale", "scale deposit" or "pretreatment scale") can accumulate within a pretreatment reactor. Once discovered, it was found that this was inhibiting the flow of the feedstock slurry through the reactor and thus through downstream stages of the process. The scale accumulation necessitated frequent halting of the process for cleaning operations and this proved to be a time-consuming and costly endeavor as the system had to be disassembled and then subjected to a high pressure water wash. The identity of the scale was unknown until investigative work revealed that it was composed of lignin.

WO 2006/128304 discloses that scale containing inorganic salts can deposit on the process equipment downstream of a pretreatment reactor. Deposition of scale occurs after the addition of alkali to adjust the pH of the acid-pretreated slurry exiting the reactor to 4-6 prior to enzymatic hydrolysis. This scale deposit contains calcium sulfate and calcium bisulfate resulting from the sulfuric acid added during pretreatment and calcium that is present in the feedstock.

Lignin is an organic compound that confers water resistance and stiffness to the fiber, as well as protection against microbial attack. Lignin differs from cellulose and hemicellulose in that it is not composed of sugar units, but rather a complex three-dimensional matrix of phenolic-propane units. Although lignin does not yield any fermentable sugars, it can be burned in the plant to generate electricity for the conversion process, thereby avoiding the use of fossil fuels. Lignin that is burned in the plant is obtained from downstream stages of the process, typically after cellulose hydrolysis by cellulase enzymes. Insolubles that remain after enzymatic hydrolysis contain insoluble lignin and can be separated from the sugars by filtration and then burned in a boiler to generate steam.

It is known to remove lignin from the lignocellulosic feedstock itself at the beginning of cellulosic conversion processes and numerous reagents have been proposed for such purpose. Examples include treatment with ethanol and water, followed by hemicellulose hydrolysis at high temperatures (WO2007/129921); delignification by pretreatment conducted with lime under oxidative conditions, followed by enzymatic hydrolysis of cellulose (US 2008/0121359), dissolution of lignin and release of monosaccharides, polysaccharides and oligosaccharides by cooking lignocellulosic feedstock with organic solvents (e.g. ethanol), followed by saccharification with cellulase enzymes and fermentation (U.S. Pat. No. 7,465,791); and aspen chip delignification with monoethanolamine (Shah et al., 1991, Applied Biochemistry and Biotechnology 28/29:99-109). Enzymatic degradation of lignin has also been investigated (Eriksson, 1993, Journal of Biotechnology 30:149-158). However, none of the foregoing references disclose the production of lignin scale, or any measures that can be taken for its prevention or removal.

EP 1,026,312 discloses a method for purposefully precipitating dissolved lignin onto pulp fibers to improve pulp yield of unbleached pulp. Such precipitation is accomplished by adding an acid into a dilute lignin stream during the washing stage of brown stock pulp. The pH of the dilute lignin stream is reduced to a level sufficient to cause the precipitation of lignin onto the pulp fiber and to increase pulp yield. However, in the process the acid concentration is low enough that caking or blockages in piping or on the pulp washer are prevented.

U.S. Pat. No. 3,546,200 discloses a method for precipitating lignin from black liquor, which is the liquid material remaining from pulpwood cooking in the soda or sulfate papermaking process. The process involves acidifying the lignin-containing black liquor to a pH of less than 4.1 and treating the mixture before a step of filtering with a hydrocarbon that enhances the precipitation.

SUMMARY OF THE INVENTION

The present invention relates to a process for treating a lignocellulosic feedstock. More specifically, the present invention provides a method for the processing of lignocellulosic feedstocks which comprises an acidic pretreatment.

It is an object of the invention to provide an improved method for the treatment of lignocellulosic feedstocks.

The present invention is based on the finding that a scale deposit was forming on the inner surface of the pretreatment reactor which, in turn, reduced slurry flow both through the pretreatment reactor and downstream stages. Characterization of the scale deposit by elemental analysis and Fourier Transform Infrared Spectroscopy (FT-IR) suggested that it was composed of lignin. Without wishing to be bound by theory, such lignin scale is thought to be formed by polymerization reactions that form a three-dimensional, highly branched network of lignin molecules of infinite molecular weight. Due to the complex chemical structure of the scale it proved difficult to dissolve, especially as the scale aged.

However, the inventors have discovered that scale removal can be carried out by treatment with alkali at elevated temperatures. Advantageously, the treatment conditions can result in high levels of scale removal within relatively short time periods. Lignin dissolution by alkali is thought to be effected by hydroxide ions, suggesting that a variety of alkali can be utilized for dissolving the scale. Regardless of the mechanism, by removing scale deposit under such conditions, downtime resulting from scale removal can be minimized, which, in turn, can significantly improve the economics of the process.

Thus, according to first aspect of the present invention, there is provided a method for processing of a lignocellulosic feedstock comprising the steps of:

a. pretreating the lignocellulosic feedstock in a pretreatment reactor with acid to make said feedstock more amenable to hydrolysis with cellulase enzymes, wherein during the pretreating, a scale deposit comprising lignin forms on the inner surface of the pretreatment reactor; and b. treating the scale deposit with an alkali solution at a temperature between about 140° C. and about 250° C.

The lignocellulosic feedstock may be selected from the group consisting of wheat straw, barley straw, corn stover, soybean stover, canola straw, oat straw, rice straw, switch grass, miscanthus, sugar cane bagasse, sugar cane straw and reed canary grass.

In one embodiment of the invention, the pretreating is conducted to hydrolyze hemicellulose present in the feedstock. The pretreating may be conducted at a temperature between about 160 and about 280° C., at a pH between about 0.4 to about 3.5 and for between about 0.05 and about 20 minutes. The acid used in the step of pretreating may be selected from the group consisting of sulfuric acid, sulfurous acid, sulfur dioxide and a combination thereof. Preferably, the acid is sulfuric acid.

According to one embodiment of the invention, the step of treating the scale is conducted at a temperature between about 160° C. and about 220° C., or between about 180° C. and 220° C.

The alkali solution used in the step of treating may be sodium hydroxide or potassium hydroxide. In one embodiment of the invention, it is sodium hydroxide. The concentration of alkali may be between 1% (w/w) and 10% (w/w).

According to a second aspect of the invention, there is provided a method for processing of a lignocellulosic feedstock comprising the steps of:

a. exposing lignocellulosic feedstock to acid in a reactor to hydrolyze at least hemicellulose present in said lignocellulosic feedstock, wherein during said exposing, a scale deposit comprising lignin forms on the inner surface of said reactor; and b. treating said scale deposit with an alkali solution at a temperature between about 140° C. and about 250° C.

According to embodiments of the second aspect of the invention, at least a portion of the cellulose present in said feedstock is hydrolyzed during exposure to said acid.

According to a further aspect of the invention, there is provided a method for reducing scale deposit that forms on process equipment during a stage of reacting a lignocellulosic feedstock with acid. The process comprises treating the scale deposit formed on the process equipment with an alkali solution at a temperature between about 140° C. and about 250° C., wherein the scale deposit comprises lignin.

During the stage of reacting the lignocellulosic feedstock with acid, at least a portion of the hemicellulose may be hydrolyzed.

It should be understood that this summary of the invention does not necessarily describe all features of the invention.

BRIEF DESCRIPTION OF THE DRAWINGS

These and other features of the invention will become more apparent from the following description in which reference is made to the appended drawings.

DETAILED DESCRIPTION

The following description is of preferred embodiments.

The feedstock for the process is a lignocellulosic material. By the term "lignocellulosic feedstock", it is meant any type of plant biomass such as, but not limited to, non-woody plant biomass, cultivated crops such as, but not limited to grasses, for example, but not limited to, C4 grasses, such as switch grass, cord grass, rye grass, miscanthus, reed canary grass, or a combination thereof, sugar processing residues, for example, but not limited to, baggase, such as sugar cane bagasse, beet pulp, or a combination thereof, agricultural residues, for example, but not limited to, soybean stover, corn stover, rice straw, sugar cane straw, rice hulls, barley straw, corn cobs, wheat straw, canola straw, oat straw, oat hulls, corn fiber, or a combination thereof, forestry biomass for example, but not limited to, recycled wood pulp fiber, sawdust, hardwood, for example aspen wood, softwood, or a combination thereof. Furthermore, the lignocellulosic feedstock may comprise cellulosic waste material or forestry waste materials such as, but not limited to, newsprint, cardboard and the like. Lignocellulosic feedstock may comprise one species of fiber or, alternatively, lignocellulosic feedstock may comprise a mixture of fibers that originate from different lignocellulosic feedstocks. In addition, the lignocellulosic feedstock may comprise fresh lignocellulosic feedstock, partially dried lignocellulosic feedstock, fully dried lignocellulosic feedstock, or a combination thereof.

Lignocellulosic feedstocks comprise cellulose in an amount greater than about 20%, more preferably greater than about 30%, more preferably greater than about 40% (w/w). For example, the lignocellulosic material may comprise from about 20% to about 50% (w/w) cellulose, or more, or any amount therebetween, for example, but not limited to 20, 22, 24, 26, 28, 30, 32, 34, 36, 38, 40, 42, 44, 46, 48 and 50% (w/w) cellulose. The lignocellulosic feedstock also comprises lignin in an amount greater than about 10%, more typically in an amount greater than about 15% (w/w). The lignocellulosic feedstock may also comprise small amounts of sucrose, fructose and starch.

Examples of preferred lignocellulosic feedstocks include (1) agricultural wastes such as corn stover, wheat straw, barley straw, canola straw, oat straw, rice straw and soybean stover; and (2) grasses such as switch grass, miscanthus, cord grass and reed canary grass.

The lignocellulosic feedstock may be first subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, a hammer mill. Feedstock may be reduced to particles having an average length of about 1/16 to about 1 in., or any amount therebetween; for example, the length of the particles may be about 1/16, 1/8, 3/16, 1/4, 5/16, 3/8, 7/16, 1/2, 9/16, 5/8, 11/16, 3/4, 13/16, 7/8 or 1 in., or any amount therebetween. Chemical action typically includes the use of heat (often steam), acids and solvents. Several chemical and mechanical pretreatment methods are well known in the art. The preferable equipment for the particle size reduction is a hammer mill, a refiner or a roll press as disclosed in WO 2006/026863, which is incorporated herein by reference.

The pretreatment is employed to increase the susceptibility of the lignocellulosic feedstock to hydrolysis by cellulase enzymes. For example, the pretreatment may be carried out to hydrolyze the hemicellulose, or a portion thereof, that is present in the lignocellulosic feedstock to monomeric sugars, for example xylose, arabinose, mannose, galactose, or a combination thereof. In one embodiment, the pretreatment is designed so that complete or significant hydrolysis of the hemicellulose but limited conversion of cellulose to glucose occurs. Preferably, the pretreatment is carried out to minimize the degradation of xylose and the production of furfural. For example, less than about 10% of the xylan in the feedstock may be converted to furfural in pretreatment and the amount of furfural produced in pretreatment is less than about 5 wt % of the amount of glucose produced in the pretreatment and enzyme hydrolysis step. The cellulose is hydrolyzed to glucose in a subsequent step that uses cellulase enzymes.

During the pretreatment, typically an acid concentration from about 0.02% (w/w) to about 2% (w/w), or any amount therebetween, is used for the treatment of the lignocellulosic feedstock.

The process would typically be a continuous process, meaning that the lignocellulosic feedstock is pumped through the pretreatment reactor continuously. Continuous acid pretreatment is familiar to those skilled in the art (see for example U.S. Pat. Nos. 5,536,325 and 4,237,226). However, scale build-up could potentially be a problem in batch processes as well. Accordingly, batch processes are also included within the scope of the invention.

Preferably, the feedstock is slurried in liquid prior to pretreatment. The feedstock may be slurried at a temperature of between about 40° C. and about 100° C., or any temperature range therebetween. For example, the feedstock may be at about 40, 45, 50, 55, 60, 65, 70, 75, 80, 85, or 90° C., or any temperature therebetween. The hot water may be recirculated from elsewhere in the process, or heated immediately prior to addition of the feedstock.

The pretreatment temperature will generally depend on the retention time, acid concentration, feedstock used and degree of treatment required. For example, temperature may be between about 160° C. and about 280° C., or any temperature therebetween. For example, the temperature may be about 160, 165, 170, 175, 180, 185, 190, 195, 200, 205, 210, 215, 220, 225, 230, 235, 240, 245, 250, 255, 260, 265, 270, 275, 280° C., or subvalues thereof.

The concentration of the slurry entering the pretreatment reactor may be about 5% to 40% (w/w) feedstock solids, or any amount therebetween. In a further embodiment of the invention, the concentration of the slurry entering the pretreatment system is about 4% to 32% (w/w) feedstock solids, or any amount therebetween. The condensation of steam in the heating of the slurry decreases the solids concentration to about 80% of its initial value. Thus, the feed to the pretreatment reactor is typically about 3% to about 27% (w/w) feedstock solids, or any amount therebetween.

The pretreatment may be carried out under pressure. For example, the pressure during pretreatment may be between about 50 and about 1000 psig or between about 75 and about 700 psig, or any pressure range therebetween. That is, the pretreatment may be carried out at 50, 100, 75, 150, 200, 250, 300, 350, 400, 450, 500, 550, 600, 650, 700, 750, 800, 850, 900, 950 or 1000 psig, or subvalues thereof.

The feedstock may be heated with steam during pretreatment. In a non-limiting example, one method to carry this out is to use low pressure steam to partially heat the feedstock, which is then pumped to a heating train of several stages.

An alternative to pumping the feedstock directly into a heating train is to leach the salts, proteins, and other impurities out of the feedstock, as taught by Griffin et al. in WO 02/070753 (incorporated herein by reference). The feedstock may then be pumped into the heating train.

Without being limiting, the heating train may comprise at least one stage of steam heating of the feedstock, with subsequent heating stages employing successively higher temperatures. In a non-limiting example, about 2 to 8 stages, or any amount therebetween, may be used; for example 2, 3, 4, 5, 6, 7 or 8. Preferably, the number of stages is high enough to provide the ability to use steam at the different pressures that are available, but low enough so the cost of pumps and the complexity is reasonable.

Examples of acids that can be used in the process include those selected from the group consisting of sulfuric acid, sulfurous acid, sulfur dioxide and a combination thereof. The preferred acid is sulfuric acid. The acid may be stored as a 93% w/w concentrate. The amount of acid added may vary, but should be sufficient to achieve a final concentration of acid of about 0.02% to about 2% w/w, or any amount therebetween. The resulting pH of the feedstock is about pH 0.4 to about pH 3.5, or any pH range therebetween. For example, the pH of the slurry may be between about 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5 or subvalues thereof.

As would be appreciated by those of skill in the art, measurement of pH presents a challenge at the elevated temperature and pressure of a pretreatment system and pH probes at these conditions are not reliable. For the purpose of this specification, the pH of pretreatment is the pH value measured by adding acid and water (and other liquids if present) to the feedstock at a temperature of 25° C. at the concentrations present at the entrance to the pretreatment reactor.

The pretreatment reactor may be a cylindrical pipe to convey a plug flow of feedstock slurry therethrough. The retention time in the pretreatment reactor will vary depending on the temperature, acid concentration, feedstock used, and the degree of treatment desired. For example, the slurry could be retained in the pretreatment reactor for about 0.05 to about 20 minutes, or for about 0.05 to about 10 minutes, or any time therebetween. That is, the retention time may be about 0.05, 0.1, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, minutes or subvalues thereof.

The pretreatment reactor may be designed to maintain a uniform or a plug flow of the feedstock. In one embodiment of the invention, the pretreatment is conducted so that there is minimal channeling of solids or liquid. If steam is used, a valve may be used at the exit of the pretreatment reactor to maintain a back pressure necessary to maintain the steam pressure at the desired level.

During acid pretreatment, a solid deposit was found to accumulate on the inner surface of the pretreatment reactor. Inductive coupled plasma atomic emission spectroscopy analyses of the scale were performed and when the results were compared to the available literature data for lignin, significant similarities were found (see Example 1). In addition, FT-IR was used to compare the scale material to alkali lignin extracted from the wheat straw. The results showed that the two had very similar characteristics (see Example 1).

It is also possible that scale deposition could result in processes that hydrolyze the lignocellulosic feedstock in a single step with acid. Such processes utilize harsher conditions than pretreatment to effect hydrolysis of both the hemicellulose and cellulose components of the feedstock.

The scale deposit is thought to be formed by lignin polymerization reactions. Without being limited by theory, lignin present in the lignocellulosic feedstock is depolymerized during acid pretreatment. This is thought to produce lower molecular weight soluble lignin, some of which subsequently precipitates on the reactor walls, where it forms scale. Periodically, pretreatment must be halted to remove the scale build-up, as the accumulation would eventually block the flow of slurry through the process. The lignin scale that deposits on the pretreatment reactor is insoluble in water.

The lignin scale is removed by treatment with alkali at elevated temperatures. In one exemplary embodiment of the invention, the temperature is between about 120° C. and about 250° C., or between about 140° C. and about 220° C., or between about 160° C. and about 220° C., or between about 180° C. and about 220° C. or any temperature range therebetween. For example, the alkali treatment may be conducted at a temperature of about 140, 145, 150, 155, 160, 165, 170, 175, 180, 185, 190, 195, 200, 205, 210, 215, 220, 225, 230, 235, 240, 245, 250° C., or subvalues thereof.

The mechanism for dissolution of lignin scale by alkali is thought to occur via the cleavage of ether bonds by hydroxide. Thus, the alkali used in the practice of the invention can be any chemical that generates hydroxide in solution at sufficient levels under the treatment conditions selected to cause dissolution or softening of the scale.

Non-limiting examples of alkali that may be used in the practice of the invention include those selected from the group consisting of sodium hydroxide, potassium hydroxide, ammonia, ammonium hydroxide, potassium carbonate, potassium bicarbonate, sodium carbonate and sodium bicarbonate. In one embodiment of the invention, the alkali is sodium hydroxide or potassium hydroxide. In yet another embodiment of the invention, the alkali is sodium hydroxide.

There are various factors that may influence the rate at which the scale is removed from the pretreatment reactor. For example, the longer the scale is exposed to acidic pretreatment conditions, the more it hardens (also referred to herein as "aging" of the scale) and becomes increasingly resistant to dissolution by alkali. Variables that may be adjusted to achieve a desired level of scale dissolution include the concentration of alkali and the exposure time of the scale to the alkali during the treatment. However, it should be understood that complete dissolution of the scale is not required. That is, it is sufficient to soften the scale with the alkali treatment, which then allows it to be physically removed by the flow of liquid through the system.

For reasons of economics, the pretreatment run time is preferably as long as possible before scale build-up is removed or significantly reduced. However, without being limiting, it is preferable that scale build-up is removed before it accumulates to such an extent that the operation must be shut down. For example, the pretreatment run time may be as long as 140 hours before scale removal is effected. Alternatively, scale removal could be effected after a run time of only one to two days, in which case the alkali treatment could be milder. In one embodiment of the invention, the pretreatment run time before scale removal is about 12 to about 140 hours, about 24 to about 140 hours, or about 50 to about 140 hours.

During cleaning of the pretreatment reactor to reduce scale, the feedstock slurry could be re-directed to a second pretreatment reactor and pretreated therein. By re-directing the feedstock in this manner, any downtime associated with the alkali cleaning is eliminated.

In another embodiment of the invention, the incoming feedstock slurry is directed to a closed recirculation loop upstream of the pretreatment reactor. After redirecting the feedstock slurry in this manner, alkali treatment can commence downstream of the circulation loop. The alkali treatment may be effected by an online caustic wash system comprising a reservoir of sodium hydroxide and a pump. Caustic from the reservoir is introduced to the pretreatment system upstream of the pretreatment reactor and pumped through the pretreatment reactor and then to waste water treatment, or re-used. If steam injection is carried out prior to acid pretreatment (see for example, WO 2006/034590, Foody et al., which is incorporated herein by reference), the caustic can be introduced into the system upstream of the steam addition point(s). By introducing caustic at this point, existing equipment can be utilized to heat the caustic to the elevated temperatures employed in accordance with the invention. Alternatively, steam can be introduced to a line in the caustic wash system itself. After alkali cleaning, the feedstock slurry is re-directed to the pretreatment reactor and pretreatment of the feedstock can recommence.

In those embodiments employing sodium hydroxide or potassium hydroxide for the alkali treatment, the percent of alkali in the solution added to the pretreatment reactor may be greater than about 1% (w/w). For example, the percent of sodium hydroxide or potassium hydroxide may be between about 1% and about 10% (w/w), or between about 2% and about 10% (w/w), or between about 4% and about 10% (w/w), or between about 5% and about 10% (w/w). Concentrations higher than 10% (w/w) are included within the scope of the invention, although, in practice, the expense of the alkali limits the use of concentrations that are higher than this.

Without being limiting, it is especially advantageous if the duration of the alkali treatment is as short as possible to reduce the length of the downtime associated with the scale removal. Thus, in exemplary embodiments of the invention, the alkali treatment is harsh enough so that the lignin scale is removed in less than about 10 hours. For example, the duration of the alkali treatment may be less than about 10, 9, 8, 7, 6, 5, 4, 3, 2 or 1 hour(s). In one embodiment of the invention, the alkali treatment is conducted for between about 2 hours and about 6 hours, or between about 3 hours and about 5 hours.

Lignin scale may also deposit on process equipment upstream or downstream of the pretreatment reactor, in addition to that formed on the pretreatment reactor itself. That is, any process equipment exposed to lignocellulosic feedstock, which is reacted with acid, is prone to scale deposits comprising lignin. Thus, the present invention includes within its scope a method for reducing lignin scale deposit that forms on process equipment exposed to feedstock under acidic reaction conditions by utilizing the alkali treatment as described previously. Process equipment prone to scale deposit comprising lignin includes, but is not limited to, flash vessels, steam mixers, plug flow reactors, vertical reactors, horizontal reactors, valves, pipes and pumps.

The pretreatment results in a pretreated feedstock composition (e.g., pretreated feedstock slurry) that contains a soluble component including the sugars resulting from hydrolysis of the hemicellulose and solids that contain unhydrolyzed feedstock and lignin.

According to one embodiment of the invention, the soluble components of the pretreated feedstock composition are separated from the solids. The soluble fraction, which includes the sugars released during pretreatment and other soluble components, including inhibitors, may then be sent to a fermentation that converts these sugars to fermentation products.

The foregoing separation may be carried out by washing the pretreated feedstock composition with an aqueous solution to produce a wash stream, and a solids stream comprising the unhydrolyzed, pretreated feedstock. Alternatively, soluble components are separated from the solids by subjecting the pretreated feedstock composition to a solids-liquid separation, using known methods such as centrifugation, microfiltration, plate and frame filtration, cross-flow filtration, pressure filtration, vacuum filtration and the like. Optionally, a washing step may be incorporated into the solids-liquids separation. The separated solids, which contain cellulose, may then be sent to enzymatic hydrolysis with cellulase enzymes in order to convert the cellulose to glucose. The resultant glucose-containing stream may then be fermented to ethanol, butanol or other fermentation products.

Alternatively, the pretreated feedstock composition is not subjected to a separation step to remove sugars released during pretreatment. That is, the enzymatic hydrolysis to convert cellulose to glucose is conducted in the presence of sugars released during the pretreatment. In such embodiment, after hydrolysis of cellulose by cellulase enzymes, glucose, xylose, galactose, mannose, arabinose, fucose and rhamnose will typically be present.

Regardless of whether or not a soluble fraction is removed from the pretreated feedstock, the pH of the pretreated feedstock is typically adjusted to a pH between about 4 and about 6 prior to hydrolysis with cellulase enzymes. Cellulase enzymes exhibit high activity in this range, although the pH can be higher if alkalophilic cellulases are used.

The enzymatic hydrolysis can be carried out with any type of cellulase enzymes capable of hydrolyzing the cellulose to glucose, regardless of their source. Among the most widely studied, characterized and commercially produced cellulases are those obtained from fungi of the genera *Aspergillus*, *Humicola*, and *Trichoderma*, and from the bacteria of the genera *Bacillus* and *Thermobifida*. The cellulases typically comprise one or more CBHs, EGs and β-glucosidase enzymes and may additionally contain hemicellulases, esterases and swollenins (See Lynd et al., 2002, Microbiology and Molecular Biology Reviews, 66(3):506-577 for a review of cellulase enzyme systems and Coutinho and Henrissat, 1999, "Carbohydrate-active enzymes: an integrated database approach." In Recent Advances in Carbohydrate Bioengineering, Gilbert, Davies, Henrissat and Svensson eds., The Royal Society of Chemistry, Cambridge, pp. 3-12, each of which are incorporated herein by reference).

Following cellulose hydrolysis of the pretreated feedstock slurry, any insoluble solids, including, but not limited to lignin, present in the resulting sugar stream may be removed using conventional solid-liquid separation techniques prior to any further processing. These solids may be burned to provide energy for the entire process.

The sugar stream may then be fermented by microbes to produce a fermentation broth comprising a fermentation product.

For ethanol production, the fermentation may be carried out with a *Saccharomyces* spp. yeast. Preferably, glucose and any other hexoses typically present in the sugar stream are fermented to ethanol by wild-type *Saccharomyces cerevisiae*, although genetically modified yeasts may be employed as well. For example, if pentose and hexose sugars are present, the fermentation may be performed with a recombinant *Saccharomyces* yeast that is engineered to ferment both hexose and pentose sugars to ethanol. Recombinant yeasts that can ferment the pentose sugar, xylose, to ethanol are described in U.S. Pat. No. 5,789,210, the contents of which are herein incorporated by reference. Furthermore, the pentose sugars, arabinose and xylose, may be converted to ethanol by the yeasts described in Boles et al. (WO 2006/096130, which is incorporated herein by reference).

Examples of other fermentation products included within the scope of the invention include sorbitol, butanol, 1,3-propanediol and 2,3-butanediol. Other microorganisms that may be employed in the fermentation include wild-type or recombinant *Escherichia, Zymomonas, Candida, Pichia, Streptomyces, Bacillus, Lactobacillus* and *Clostridium*.

In practice, the fermentation is performed at or near the temperature and pH optima of the fermentation microorganism. A typical temperature range for the fermentation of glucose to ethanol using *Saccharomyces cerevisiae* is between about 25° C. and about 35° C., although the temperature may be higher if the yeast is naturally or genetically modified to be thermostable. The pH of a typical fermentation employing *Saccharomyces cerevisiae* is between about 3 and about 6. The dose of the fermentation microorganism will depend on other factors, such as the activity of the fermentation microorganism, the desired fermentation time, the volume of the reactor and other parameters. It should be appreciated, however, that these parameters may be adjusted as desired by one of skill in the art to achieve optimal fermentation conditions.

The sugar stream may also be supplemented with additional nutrients required for the growth of the fermentation microorganism. For example, yeast extract, specific amino acids, phosphate, nitrogen sources, salts, trace elements and vitamins may be added to the hydrolyzate slurry to support their growth.

The fermentation may be conducted in batch, continuous or fed-batch modes with or without agitation. Preferably, the fermentation reactors are agitated lightly with mechanical agitation. A typical, commercial-scale fermentation may be conducted using a series of reactors, such as 1 to 6. The fermentation microorganisms may be recycled back to the fermentor or may be sent to distillation without recycle.

It should be understood that the hydrolysis and fermentation reactions can be conducted simultaneously in the same reactor, although it is preferred that the hydrolysis and fermentation are performed separately to achieve the optimal temperature for each process.

If ethanol or butanol is the fermentation product, distillation is typically conducted to concentrate the alcohol. The fermentation broth that is sent to distillation is a dilute alcohol solution containing solids, including unconverted cellulose, and any components added during the fermentation to support growth of the microorganisms. Microorganisms are potentially present depending upon whether or not they are recycled during the fermentation. The broth is preferably degassed to remove carbon dioxide and then pumped through one or more distillation columns to separate the alcohol from the other components in the broth. The mode of operation depends on whether the alcohol has a lower or a higher boiling point than water. Most often, the alcohol has a lower boiling point than water, as is the case when ethanol is distilled.

According to embodiments in which ethanol is concentrated, the column(s) in the distillation unit is preferably operated in a continuous mode, although it should be understood that batch processes are also encompassed by the present invention. Heat for the distillation process may be introduced at one or more points either by direct steam injection or indirectly via heat exchangers. The distillation unit may contain one or more separate beer and rectifying columns. In this case, dilute beer is sent to the beer column where it is partially concentrated. From the beer column, the vapour goes to a rectification column for further purification. Alternatively, a distillation column is employed that comprises an integral enriching or rectification section. After distillation, the water remaining may be removed from the vapour by a molecular sieve resin, by adsorption, or other azeotrope-breaking methods familiar to those of skill in the art. The vapour may then be condensed and denatured.

An aqueous stream(s) remaining after ethanol distillation and containing solids, referred to herein as "still bottoms", is withdrawn from the bottom of one or more of the column(s) of the distillation unit.

When the alcohol has a higher boiling point than water, such as butanol, the distillation is run to remove the water and other volatile compounds from the alcohol. The water vapor exits the top of the distillation column and is known as the "overhead stream".

The present invention will be further illustrated in the following examples. However, it is to be understood that these examples are for illustrative purposes only, and should not be used to limit the scope of the present invention in any manner.

EXAMPLES

Example 1

Discovery and Characterization of Pretreatment Scale

During the pretreatment, it was found that a solid deposit was accumulating along the inner surface of the pretreatment reactor, thereby disrupting the flow of the wheat straw slurry through the reactor and consequently downstream stages of the process.

Prior to pretreatment, the feedstock was reduced in size. Wheat straw was received in bales measuring 3 feet by 3 feet by 4 feet and chopped to approximately ¼ inch in size. The straw was then pretreated with sulfuric acid, which involved mixing the wheat straw with water and sending the resulting slurry to a standpipe where 93% (w/w) sulfuric acid was added to reduce the pH of the slurry to about 0.9 to 1.4. The slurry was pumped through piping heated by direct injection with 600 psig steam to reach a temperature of 170-220° C. and the heated, acidified stock was held at this temperature for 1 minute as it passed through a pretreatment reactor. Upon exiting the pretreatment reactor, the slurry was flashed through a series of flash tanks to drop the temperature to 85° C.

The entire pretreatment reactor was accumulating about 200 g of solid deposits per ton of straw. It was also found that the deposit thickness increased from the entrance to the exit of the pretreatment reactor. The scale proved difficult to dissolve and laboratory analysis showed that the pretreatment scale had very low solubility in 15% NaOH at 74° C. after 30 minutes.

Elemental analysis was performed to identify the solid deposits that were accumulating during the pretreatment operation. Scale samples were collected from the pretreatment reactor at its entrance, the middle region and exit and the C, H, N, O, S and Si weight percentages were determined by ICP-AES (Inductively Coupled Plasma Atomic Emission Spectrometry). Elemental analysis was also performed on Klason lignin (ash free basis), alkali lignin obtained from Sigma-Aldrich® (Product No. 370959), low sulfonate alkali lignin obtained from Sigma-Aldrich® (Product No. 471003), untreated wheat straw and alkali extracted lignin prepared from wheat straw using the procedure described by Hoareau et. al., 2004, Polymer Degradation and Stability, 86:567-576. These weight percentages were converted to molar ratios relative to carbon and are reported in Table 1 below.

TABLE 1

Comparison of the molar composition of lignin samples, wheat straw and pretreatment scale obtained from various locations in the pretreatment reactor

| SAMPLE | C = 1 | H | N | O | S | SILICON |
|---|---|---|---|---|---|---|
| Klason lignin, ash free basis | 1.00 | 1.02 | 0.01 | 0.35 | — | — |
| Lignin composition from Jensen et al.[1] | 1.00 | 1.10 | 0.00 | 0.29 | — | — |
| Alkali lignin from Sigma Aldrich ® | 1.00 | 1.09 | 0.01 | 0.34 | 0.01 | 0.00 |
| Alkali lignin low sulfonate from Sigma Aldrich ® | 1.00 | 1.11 | 0.01 | 0.48 | 0.03 | 0.00 |
| Alkali extracted wheat straw lignin | 1.00 | 1.09 | 0.02 | 0.44 | — | 0.00 |

TABLE 1-continued

Comparison of the molar composition of lignin samples, wheat straw and pretreatment scale obtained from various locations in the pretreatment reactor

| SAMPLE | C = 1 | H | N | O | S | SILICON |
|---|---|---|---|---|---|---|
| Untreated wheat straw | 1.00 | 1.60 | 0.01 | 0.70 | $3.8 \times 10^{-3}$ | $1.3 \times 10^{-2}$ |
| Lignin scale - entrance of reactor | | | | | | |
| Sample 1 | 1.00 | 1.01 | 0.01 | 0.25 | $2.4 \times 10^{-3}$ | — |
| Sample 2 | 1.00 | 1.03 | 0.01 | 0.22 | $8.7 \times 10^{-4}$ | $1.2 \times 10^{-3}$ |
| Lignin scale - middle region of reactor | | | | | | |
| Sample 1 | 1.00 | 1.02 | 0.01 | 0.26 | $6.6 \times 10^{-4}$ | $1.5 \times 10^{-3}$ |
| Sample 2 | 1.00 | 1.01 | 0.01 | 0.27 | — | — |
| Sample 3 | 1.00 | 1.03 | 0.01 | 0.24 | $6.3 \times 10^{-4}$ | $7.6 \times 10^{-4}$ |
| Sample 4 | 1.00 | 0.96 | 0.01 | 0.30 | $7.1 \times 10^{-4}$ | $3.8 \times 10^{-3}$ |
| Lignin scale - end portion of reactor | | | | | | |
| Sample 1 | 1.00 | 0.95 | 0.01 | 0.27 | — | $5.2 \times 10^{-3}$ |
| Sample 2 | 1.00 | 1.01 | 0.01 | 0.25 | $5.4 \times 10^{-4}$ | $2.8 \times 10^{-3}$ |
| Sample 3 | 1.00 | 0.98 | 0.01 | 0.27 | $9.9 \times 10^{-4}$ | $2.6 \times 10^{-3}$ |

[1] Jensen et al., 1998, Energy and Fuels, 12(5): 929-938

The pretreatment solid deposit C:H:O molar ratios roughly corresponded to a lignin composition referenced in the literature (Jensen et al., 1998, Energy & Fuels, 12(5):929-938), with approximately one less molecule of water per every 10 carbon atoms. Possible dehydration of lignin during pretreatment scale formation could be caused by acidolysis of β-O-4 bonds of lignin and a subsequent condensation of two lignin chains through a direct C—C linkage. Notably, the molar ratios of the scale are different from the molar ratios corresponding to untreated wheat straw.

Figure 1:
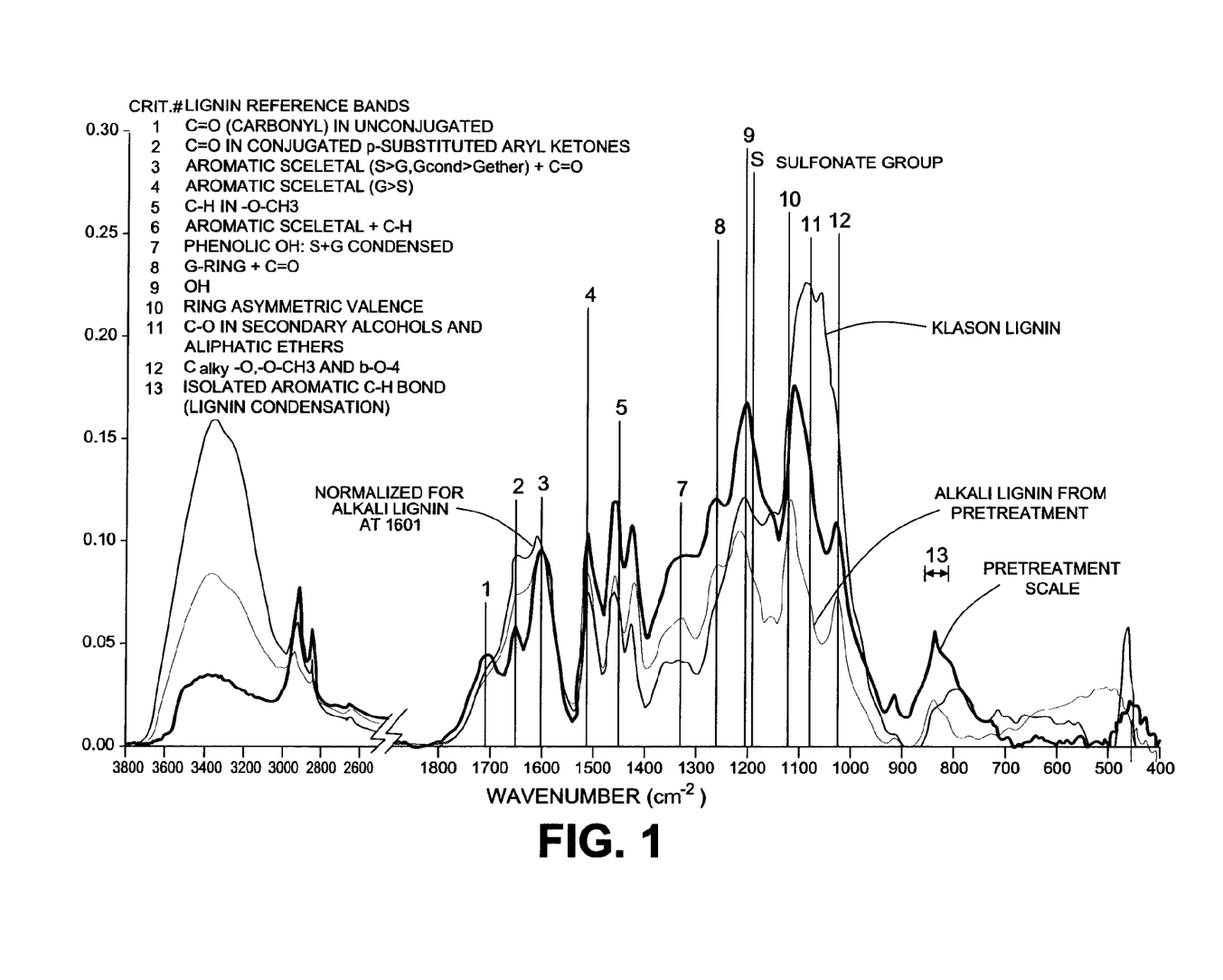
FIG. 1 is a Fourier Transform Infrared Spectroscopy (FTIR) spectra of pretreatment scale, alkali lignin extracted from pretreatment and Klason lignin.

Diamond ATR-FT-IR analysis was used to further characterize and compare different pretreatment scale materials. Recorded FT-IR spectra were compared with both the acid insoluble (Klason) lignin and the alkali lignin extracted from the wheat straw. Notably, all the pretreatment deposits were showing the same characteristic alkali lignin bands with different intensities (FIG. 1). The pretreatment reactor scale FT-IR spectra showed no additional functional groups that could be identified, except the typical lignin bands (aromatic, syringyl and guaiacyl rings, OH, C—C, C—H, C—O, C═O, O—CH3 and β-O-4). This information, together with the elemental analysis data, confirmed that lignin was the basic building block of all the pretreatment deposits.

Example 3

The Effect of Temperature on the Dissolution of Lignin Scale by Alkali

Scale was collected from a pretreatment reactor. The scale used in the dissolution experiment was harvested from a run that was estimated to be 140 hours in duration and that plugged the pretreatment reactor. This scale was found to be very hard and brittle.

After drying, 0.7 g of scale previously ground in a coffee grinder and 14 g of 4% or 10% (w/w) NaOH was added to a lab bomb reactor (¾ inch opening outer diameter; ⅝ inch inner diameter). The bomb was sealed tightly at both ends and then submerged in a hot oil bath set at a specified temperature. The reaction was carried out in the oil bath for two hours at temperatures of 120, 140, 160, 180, 200 and 220° C. with either 4% or 10% (w/w) NaOH. To quench the reaction, the bombs were carefully removed from the oil bath and submerged into a bucket of cold water for 1 minute. Complete scale dissolution was achieved at 220° C. with 10% NaOH for 2 hours. The maximum possible soluble lignin in the filtrate was determined by measuring the absorbance with a UV/Vis spectrophotometer set at 340 nm and using an extinction coefficient of 9.9 L/g-cm. This value was used comparatively throughout the experiments to calculate the relative percent of scale dissolved.

Figure 2A:
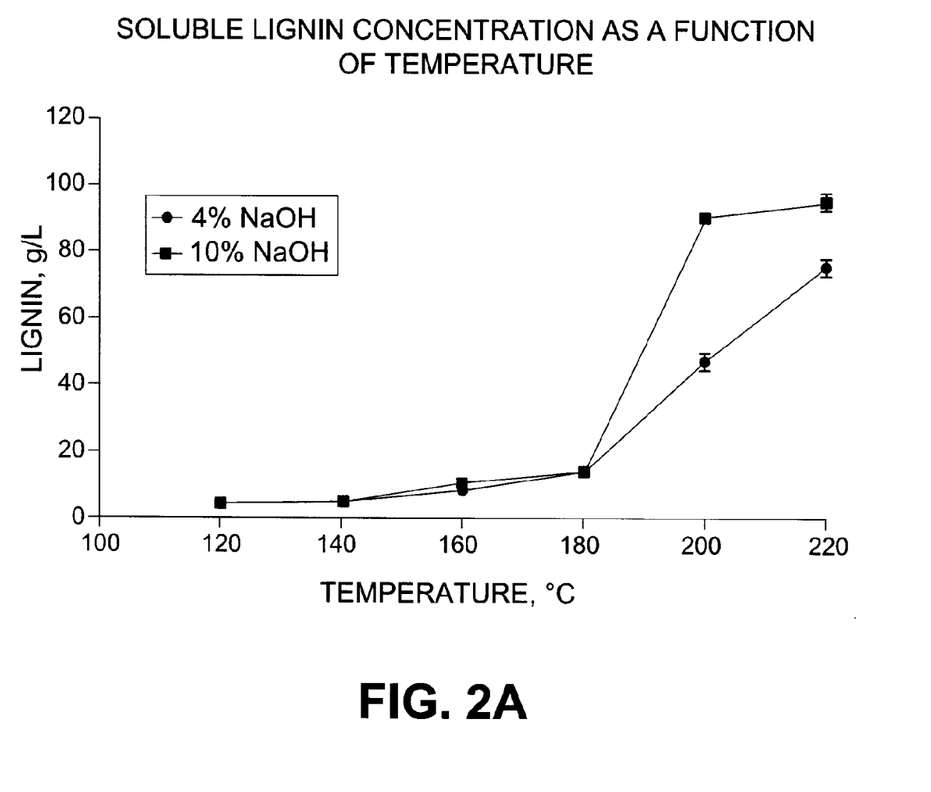
FIGS. 2A and 2B are graphs showing the soluble lignin concentration (FIG. 2A) and the dissolution of pretreatment scale (FIG. 2B) in 4% NaOH and 10% NaOH as a function of temperature. In each instance, the dissolution time with NaOH was two hours.
Figure 2B:
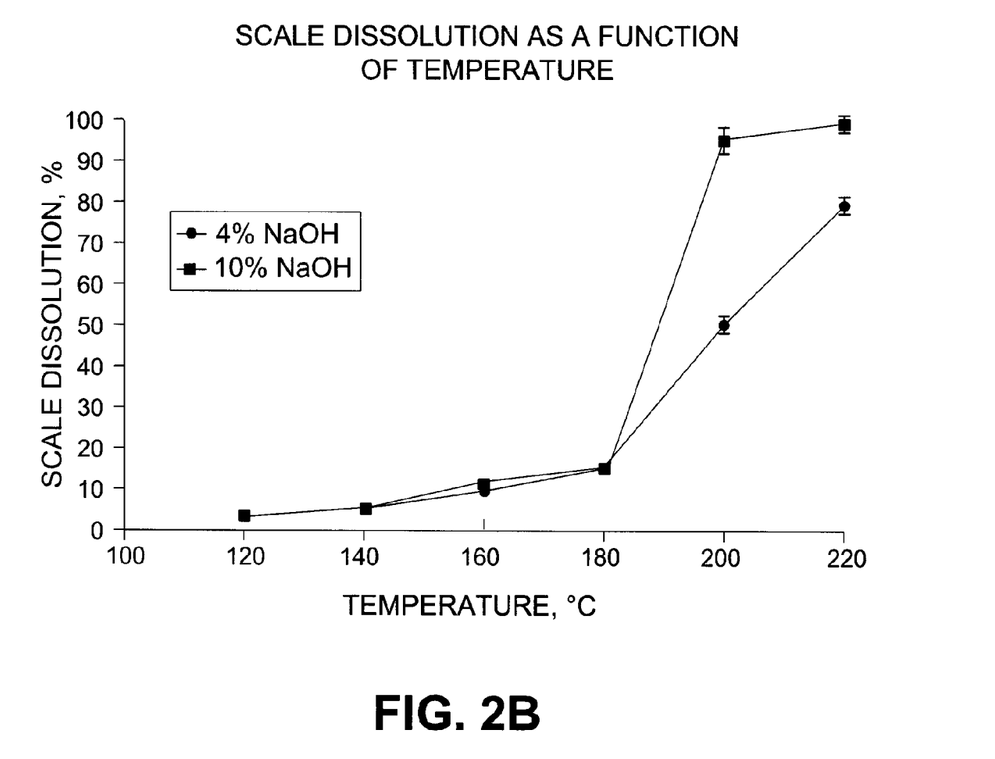

The extent of scale dissolution was found to increase significantly at temperatures above 180° C. (FIGS. 2A and 2B). Error bars plotted represent one standard deviation of duplicate assays. At temperatures between 120° C. and 180° C., the scale dissolution was less than 20% for treatments with both 4% (w/w) NaOH and 10% (w/w) NaOH, while at 200° C., the scale dissolution was about 50% using the 4% (w/w) NaOH solution and about 95% for the 10% (w/w) NaOH solution. At 220° C., the scale dissolution was about 80% with the 4% (w/w) NaOH solution and 100% with the 10% (w/w) NaOH solution.

Thus, without intending to being limiting, the alkali treatment is preferably carried out at a temperature above 180° C. Such high temperatures are particularly advantageous if the scale is difficult to dissolve, as was found with the scale resulting from this run. However, it should be appreciated that lower temperatures could be utilized, for example, if the exposure time to the alkali was increased or if the scale resulted from a shorter pretreatment run.

Example 4

The Effects of Scale Aging on Dissolution with Alkali

In order to understand the effect of aging the scale on its resistance to dissolution using caustic treatment, a scale that was harvested shortly after a 20 hour pretreatment run was cooked for different lengths of time to simulate pretreatment conditions with sulfuric acid.

Aging the scale involved adding 0.7 g of scale previously ground in a coffee grinder and 14 g of $H_2SO_4$ (pH 1.5) to ten lab bomb reactors (¾ inch opening outer diameter; ⅝ inch inner diameter). Prior to weighing, the scale was exposed to air overnight to allow the moisture to evaporate.

The scale was then cooked in the bombs for 2, 4, 7, 8 and 10 days in a bench top oven at 200° C. At the end of the cooking time, two bombs were removed from the oven and the aged scale was recovered by filtration and left to dry overnight in a fume hood. The dry scale was used to carry out the scale dissolution tests.

A two hour dissolution test with 4% NaOH at 200° C. was performed on all the aged scales. This was carried out by adding 0.7 g of the aged scale to a bomb reactor (¾ inch opening outer diameter; ⅝ inch inner diameter). The caustic solution (14 g) was then transferred to the bomb. The bomb was sealed tight at both ends and then submerged into a hot oil bath set at 200° C. To quench the reaction, the bombs were carefully removed from the oil bath and submerged into a bucket of cold water for 1 minute.

It was observed that the longer the scale was aged, the darker in colour it became. At the end of the dissolution, the contents of the bombs were transferred to a vacuum filter where the filtrate and solids were collected. The soluble lignin in the filtrate was determined by measuring the absorbance with a UV/Vis spectrophotometer set at 340 nm and using an extinction coefficient of 9.9 L/g-cm.

To calculate the maximum possible amount of dissolved scale, the soluble lignin concentration was determined for a fixed amount of scale dissolved completely using a caustic treatment at 220° C. with 10% NaOH for 2 hours.

Figure 3:
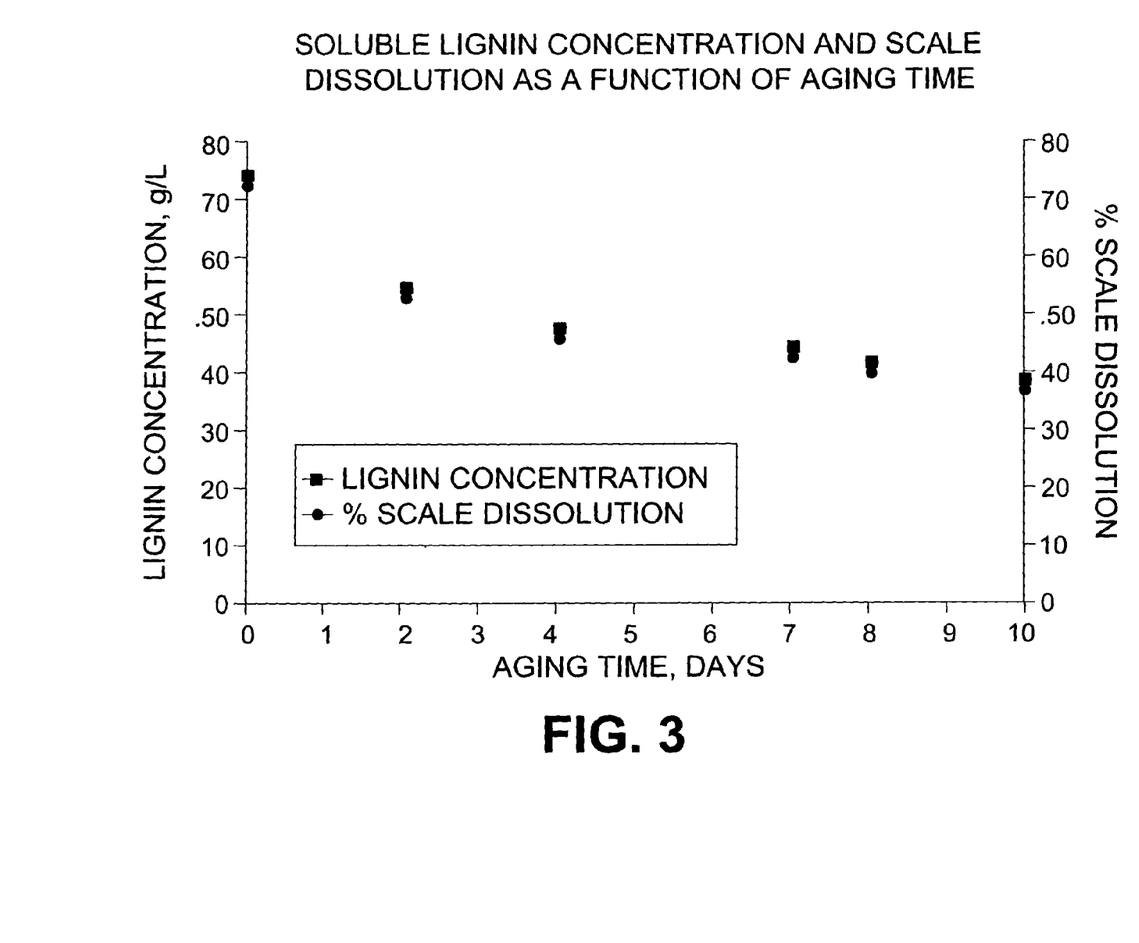
FIG. 3 is a graph showing the soluble lignin concentration and scale dissolution as a function of aging time of the pretreatment scale using a dissolution treatment carried out for two hours with 4% NaOH at 200° C.

The results of the dissolution test are shown in FIG. 3. As the aging time increases, the amount of soluble lignin after the caustic treatment decreases, which demonstrates that the longer the pretreatment, the more resistant to dissolution the scale becomes.

The invention claimed is:

1. A method for processing of a lignocellulosic feedstock comprising the steps of:
    a. pretreating said lignocellulosic feedstock with acid in a pretreatment reactor to make said feedstock more amenable to hydrolysis with cellulase enzymes, wherein during said pretreating, a lignin scale deposit forms on the inner surface of said pretreatment reactor; and
    b. treating said lignin scale deposit with an alkali solution at a temperature between about 140° C. and about 250° C.

2. The method according to claim 1, wherein the step of treating is conducted at a temperature between about 160° C. and about 220° C.

3. The method according to claim 2, wherein the step of treating is conducted at a temperature between about 180° C. and about 220° C.

4. The method according to claim 1, wherein the alkali solution used in the step of treating is sodium hydroxide or potassium hydroxide.

5. The method according to claim 4, wherein the alkali solution used in the step of treating is sodium hydroxide.

6. The method according to claim 5, wherein the concentration of the sodium hydroxide is between about 1 and about 10 wt %.

7. The method according to claim 1, wherein the pretreating is conducted to hydrolyze hemicellulose present in said feedstock.

8. The method according to claim 1, wherein the pretreating is conducted at a temperature between about 160 and about 280° C., at a pH between about 0.4 to about 3.5 and for a time duration of between about 0.05 and about 20 minutes.

9. The method according to claim 1, wherein the acid used in the step of pretreating is selected from the group consisting of sulfuric acid, sulfurous acid, sulfur dioxide and a combination thereof.

10. The method according to claim 9, wherein the acid used in the step of pretreating is sulfuric acid.

11. A method for processing of a lignocellulosic feedstock comprising the steps of:
    a. exposing lignocellulosic feedstock to acid in a reactor to hydrolyze at least hemicellulose present in said lignocellulosic feedstock, wherein during said exposing, a lignin scale deposit forms on the inner surface of said reactor; and
    b. treating said lignin scale deposit with an alkali solution at a temperature between about 140° C. and about 250° C.

12. A method for processing of a lignocellulosic feedstock comprising the steps of:
    a. pretreating said lignocellulosic feedstock with acid in a first pretreatment reactor to make said feedstock more amenable to hydrolysis with cellulase enzymes, wherein during said pretreating, a lignin scale deposit forms on the inner surface of said first pretreatment reactor; and
    b. treating said lignin scale deposit in the first pretreatment reactor with an alkali solution at a temperature between about 140° C. and about 250° C., wherein during said treating, incoming lignocellulosic feedstock is re-directed to a second pretreatment reactor and pretreated therein.

13. The method according to claim 12, wherein the alkali solution used in the step of treating is sodium hydroxide or potassium hydroxide.

14. A method for reducing lignin scale deposit that forms on process equipment during a stage of reacting a lignocellulosic feedstock with acid, which process comprises treating the lignin scale deposit formed on said process equipment with an alkali solution at a temperature between about 140° C. and about 250° C.

15. The method according to claim 14, wherein during the stage of reacting the lignocellulosic feedstock with acid, at least a portion of the hemicellulose is hydrolyzed.

16. The method according to claim 14, wherein the alkali solution used in the step of treating comprises potassium hydroxide.

17. The method according to claim 14, wherein the alkali solution used in the step of treating comprises sodium hydroxide.

18. The method according to claim 17, wherein the concentration of the sodium hydroxide is between about 1 and about 10 wt %.

19. The method according to claim 14, wherein the process equipment is selected from the group consisting of a flash vessel, a steam mixer, a reactor, a valve, a pipe and a pump.

* * * * *